United States Patent [19]
Nishino et al.

[11] Patent Number: 5,628,844
[45] Date of Patent: *May 13, 1997

[54] METHOD FOR MAKING A TOPSHEET FOR USE IN DISPOSABLE BODY FLUID ABSORPTIVE ARTICLES

[75] Inventors: Kazunari Nishino, Ohtake; Shigeyuki Motomura, Yamaguchi-ken; Shizuo Shimizu, Tokyo; Takamitsu Igaue, Kawanoe; Tsutomu Kido, Kawanoe; Hisashi Takai, Kawanoe, all of Japan

[73] Assignees: Mitsui Petrochemical Industries, Ltd., Tokyo; Uni-Charm Corporation, Ehime-ken, both of Japan

[*] Notice: The term of this patent shall not extend beyond the expiration date of Pat. No. 5,522,811.

[21] Appl. No.: 351,196

[22] Filed: Nov. 30, 1994

Related U.S. Application Data

[62] Division of Ser. No. 210,997, Mar. 21, 1994, Pat. No. 5,449,352.

[30] Foreign Application Priority Data

Mar. 24, 1993 [JP] Japan ................................ 5-89101

[51] Int. Cl.$^6$ .......................... B32B 31/00; A61F 13/15
[52] U.S. Cl. .................... 156/62.4; 156/167; 156/290; 428/138
[58] Field of Search ....................... 156/167, 62.4, 156/290; 19/148, 296, 301, 302, 308; 428/131, 134, 137, 138

[56] References Cited

U.S. PATENT DOCUMENTS

| | | |
|---|---|---|
| 4,397,644 | 8/1983 | Matthews et al. .................. 604/370 |
| 4,634,440 | 1/1987 | Widlund et al. . |
| 4,741,941 | 5/1988 | Englebert et al. . |
| 5,171,238 | 12/1992 | Kajander . |
| 5,522,811 | 6/1996 | Igaue et al. . |

FOREIGN PATENT DOCUMENTS

| | | |
|---|---|---|
| 0587118A1 | 3/1994 | European Pat. Off. . |
| 4-152945 | 5/1992 | Japan ........................... 604/366 |
| A-04166151 | 6/1992 | Japan . |
| WO93/11725 | 6/1993 | WIPO . |

*Primary Examiner*—Michael W. Ball
*Assistant Examiner*—Sam Chuan Yao
*Attorney, Agent, or Firm*—Lowe, Price, LeBlanc & Becker

[57] ABSTRACT

A topsheet for use in body fluid absorptive articles is so improved that collapse and clogging of liquid passages therein may be reliably avoided. The topsheet includes an upper sheet, provided with skin-contacting areas and liquid passages, and a lower sheet provided with skin-non-contacting areas, areas welded to the liquid passages, and exposed areas. The exposed areas are welded to each of the liquid passages around lower openings thereof so as to protect the liquid passage against collapse and clogging. The exposed areas define a skin-contacting surface which rises up into each of the liquid passages without extending above the upper surface of the skin-contacting areas. The upper sheet cooperates with the lower sheet to define cavities extending in the direction of the topsheet thickness.

1 Claim, 5 Drawing Sheets

METHOD FOR MAKING A TOPSHEET FOR USE IN DISPOSABLE BODY FLUID ABSORPTIVE ARTICLES

This application is a division of application Ser. No. 08/210,997 filed Mar. 21, 1994, now U.S. Pat. No. 5,449,352.

BACKGROUND OF THE INVENTION

The present invention relates to a liquid-permeable topsheet for use in disposable body fluid absorptive articles such as sanitary napkins, disposable diapers and training pants.

In liquid-permeable topsheets used for body fluid absorptive articles, a technique is well known to make the topsheet from plastic film or nonwoven fabric, and to provide it with liquid passages each extending from top to bottom thereof. The upper surface of the sheet is in contact with the wearer's skin. Lower openings of the respective liquid passages are in contact with an absorbent core so that capillary action occurring within each liquid passage may be utilized to transfer excreted body fluids toward the absorbent core.

Japanese Patent Publication No. 1982-17081 discloses a technique wherein a topsheet made of polyethylene film is provided with conically tapered capillaries having lower ends arranged to be in close contact with an absorbent core.

According to a technique disclosed by Japanese patent application Disclosure No. 1985-259261, a topsheet made of plastic film is provided with cylindrical liquid passages with their lower ends extending into an absorbent core. Such cylindrical liquid passages are more stable and therefore less deformable than conical liquid passages under a large load in the axial direction.

Japanese patent application Disclosure No. 1992-152945 discloses a technique according to which there is provided a high density area or rib continuously surrounding lower openings of respective liquid passages. This technique certainly stabilizes an opening of each liquid passage against deformation as well as collapse and allows the body fluids to be effectively transferred toward an absorbent core.

U.S. Pat. No. 4,741,941 discloses a method for making a topsheet provided with liquid passages utilizing the manufacturing process for melt blown nonwoven fabric or span bond nonwoven fabric. It is also proposed by this patent that woody pulp is fed onto the lower side of the topsheet and a combination thus integrated is used for absorptive articles.

Japanese patent application Disclosure No. 1981-11058 discloses a technique according to which an upper sheet made of hydrophobic material is integrally combined with a lower sheet made of hydrophilic material so that the lower sheet partially rises up through a layer of the upper sheet until it is exposed beyond the upper surface of the upper sheet and thereby a plurality of liquid-permeable spots are formed. According to this technique, the aforesaid liquid passages may be replaced by these liquid-permeable spots to introduce the body fluids toward an absorbent core.

The soft touch is generally essential to the topsheet and the conventional topsheets as disclosed by the above-identified Patent Publication and Disclosure are also made of thin and soft materials from such a viewpoint. With a negative consequence, however, the conical liquid passages disclosed by the Japanese Patent Publication No. 1982-17081 as well as the cylindrical liquid passages disclosed by the Japanese patent application Disclosure No. 1985-259261 are disadvantageous in that the lower openings, i.e., free ends of these liquid passages are liable to be deformed, so that the liquid passages readily collapse, for example, even under a relatively low pressure against the wearer and the body fluids are often prevented thereby from being smoothly transferred toward the absorbent core. While stability of each liquid passage against a compressive force axially exerted on the liquid passage can be more or less improved, the liquid passage is still easily collapsed under a force transversely exerted on the liquid passage since, after all the liquid passage comprises soft material.

While the technique disclosed by the above-identified Japanese patent application Disclosure No. 1992-152945 may theoretically alleviate the problem of collapse, both a thickness of the topsheet and a diameter of the liquid passage are unfeasibly fine, i.e. it would not be easy to provide the previously mentioned high density area or rib continuously surrounding the lower openings of the respective liquid passages although this is one of the most important features of the disclosed technique.

The technique disclosed by U.S. Pat. No. 4,741,941 provides a soft cloth-like touch by using melt-blown nonwoven fabric, however such nonwoven fabric lacks firmness and consequently the liquid passages are liable to collapse and clog. In addition, the nonwoven fabric is in rather close contact with the pulp layer fed to and combined with the lower side of the nonwoven fabric and, when this combined material is used in the absorptive articles, a quantity of moisture once held by the pulp layer readily exudes and spreads over the upper surface of the melt-blown nonwoven fabric under body pressure of the wearer who experiences an unpleasant wetness.

The technique disclosed by Japanese patent application Disclosure No. 1981-11058 is free from apprehension that the liquid passages might be collapsed and clogged and the lower sheet visibly exposed through the upper sheet as viewed from above advantageously functions to absorb sweat when it comes in contact with the skin of the wearer, since the lower sheet is hydrophilic. However, the quantity of moisture once held by the lower sheet readily flows back toward the upper sheet under a body pressure of the wearer, since the lower sheet is in close contact with the upper sheet primarily composed of nonwoven fabric. Accordingly, this technique also has a problem that the wearer experiences an unpleasant wetness.

In view of these unsolved prior art problems, it is a principal object of the invention to provide a topsheet comprising a first sheet having a skin-contacting area and a second sheet underlying said first sheet, wherein said first sheet is provided with Liquid passages and said second sheet is welded to said first sheet around lower openings of the respective liquid passages so as to restrict possibly occurring deformation of the liquid passages, on the one hand, and spaced from the lower side of the skin-contacting area to avoid possibly occurring backflow of body fluids from the second sheet toward the first sheet, on the other hand, and thereby solve the problems encountered by the conventional topsheets.

SUMMARY OF THE INVENTION

The object set forth above is achieved, according to first aspect of the invention, with a topsheet for use in a body fluid absorptive article. The said topsheet includes a plurality of liquid passages each extending through the topsheet from an upper opening to a lower opening thereof and a skin-contacting area continuously formed around the upper openings of the respective liquid passages. The topsheet comprises a first sheet made of thermoplastic sheet and provided with said liquid passages and skin-contacting area, and a second sheet underlying said first sheet and made of nonwoven fabric of thermoplastic fibres and provided with a skin-noncontacting area opposed to said skin-contacting area, an area welded to said liquid passages along peripheral edges of their lower openings and an area exposed within said liquid passages so that inner walls of said liquid passages, said skin-contacting area and said skin-noncontacting area spaced by said liquid passages from said skin-contacting area cooperate together to define cavities extending in the direction of the topsheet thickness.

Preferably, the area exposed within said liquid passages defines skin-contacting spots rising up into the respective liquid passages but not beyond the upper surface of said skin-contacting area.

Preferably, said first sheet is hydrophobic and said second sheet is hydrophilic.

The object set forth above is achieved, according to a second aspect of the invention, by a method for making the topsheet for use in body fluid absorptive articles, said topsheet being provided with a plurality of liquid passages each extending through the topsheet from an upper opening to a lower opening thereof and a skin-contacting area continuously formed around the upper openings of the respective liquid passages. The method comprises the steps of forming the first sheer provided with said liquid passages and said skin-contacting area from a thermoplastic sheet and blowing molten fibres onto a lower side of said first sheet to form a second sheet made of melt-blown nonwoven fabric, wherein said second sheet has a skin-noncontacting area spaced from a lower surface of the skin-contacting area defined by said first sheet and an area welded to said liquid passages around their lower openings and wherein said skin-contacting area inner walls of said liquid passages and said skin-contacting area cooperate to define cavities extending in the direction of the topsheet thickness.

The object set forth above is achieved, according to a third aspect of the invention, by an apparatus to make the topsheet for use in the body fluid absorptive articles, said topsheet being provided with a plurality of liquid passages each extending through the topsheet from an upper opening to a lower opening thereof and a skin-contacting area continuously formed around the upper openings of the respective liquid passages. The apparatus comprises:

(1) at least one melt extruder exclusively to form a first sheet provided with said liquid passages and skin-contacting area;

(2) a mold against which molten fibres are blown from said melt-blow extruder exclusively for the formation of said first sheet to form melt-blown nonwoven fabric, said mold being provided with a plurality of protrusions and indents which are alternately arranged to serve as forming dies to form said nonwoven fabric with said liquid passages and a skin-contacting area and being responsive to an output of molten fibres from said melt-blow extruder exclusively used for the formation of the first sheet operate at the optimum speed;

(3) at least one melt-blow extruder exclusively used for the formation of a second sheet adapted to blow molten fibres against a lower side of said first sheet released from said mold and thereby to form said second sheet comprising melt-blown nonwoven fabric welded to the respective liquid passages around their lower openings;

(4) conveyor means to transport said first sheet toward said melt-blow extruder exclusively to for the second sheet; and (5) suction means provided in opposition to said melt-blow extruders respectively used to form the first sheet and the second sheet, respectively.

With the topsheet constructed as described above, the second sheet made of nonwoven fabric is welded to the liquid passages around their lower openings so as to restrict The deformation possibly occurring in peripheral edges of the respective lower openings. Additionally, the first sheet and the second sheet are continuous with the liquid passages around their upper and lower openings, respectively, so as to stabilize the liquid passages reliably not only against axial forces as well but also against the transverse force.

The body fluids flow into the liquid passages and reach the lower openings thereof, whereupon the body fluids permeate through the second sheet, and are then partly absorbed by spots of the absorbent core immediately underlying these lower openings, and partly diffuse laterally through the second sheet and are absorbed by the portions of the absorbent core which are in contact with the skin-noncontacting area of the second sheet. The skin-noncontacting area of the second sheet moistened by such diffusion is kept spaced from the lower side of the skin-contacting area and there is no apprehension that the backflow of the body fluids from the skin-noncontacting area toward the skin-contacting area might give the wearer an unpleasant feeling of wetness.

The second sheet is hydrophilic and, when its skin-contacting surface rising up into the liquid passages comes in contact with the skin of the wearer, the capillary action occurring between the fibres constituting this sheet functions to transfer sweat into the absorbent core.

In the method for making the topsheet of the invention comprising the first sheet and the second sheet, molten fibres are blown against the lower side of the first sheet provided with the skin-contacting area and the liquid passages to form the second sheet made of melt-blown nonwoven fabric, and thereby the second sheet is welded to the first sheet around the lower openings of the respective liquid passages and The skin-noncontacting area is kept spaced from the lower side of the skin-contacting area. The second sheet is visibly exposed within the respective liquid passages when the first sheet is viewed from right above.

The apparatus for continuously making the topsheet of the invention comprising the first sheet and The second sheet comprises the melt-blow extruder exclusively used to form a first sheet, the mold being responsive to the output of molten fibres from The melt-blow extruder to operate at the optimum speed, the melt-blow extruder exclusively used form the second sheet on the lower side of the first sheet, and conveyor means for the first sheet.

BRIEF DESCRIPTION OF THE DRAWINGS

The invention will be described by way of example in reference with the accompanying drawings, in which.

PREFERRED EMBODIMENTS OF THE INVENTION

Figure 1:
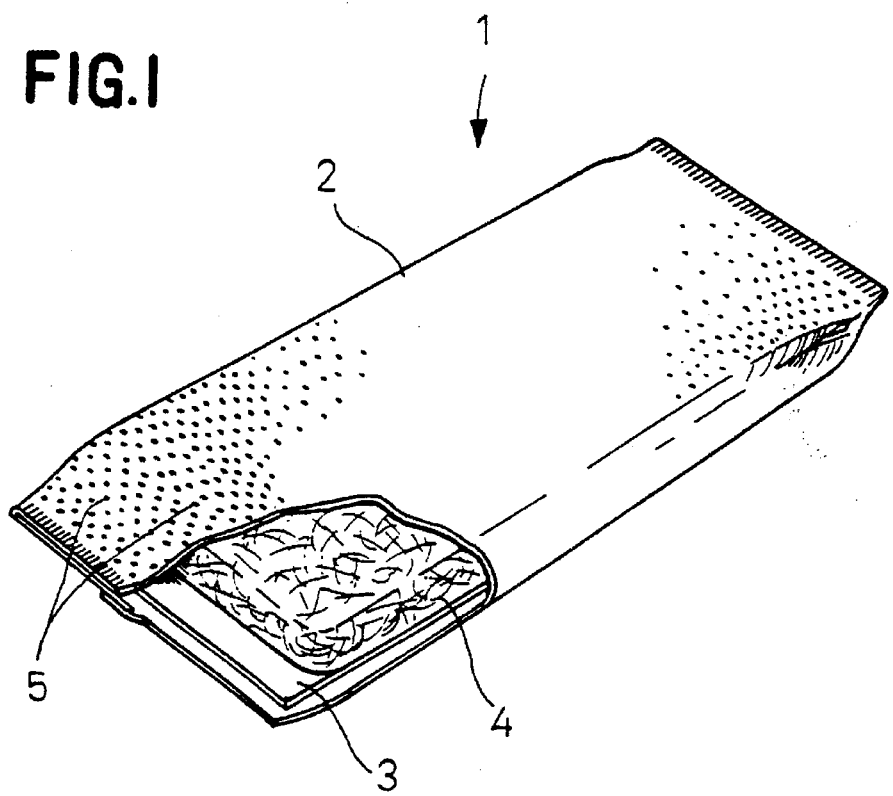
FIG. 1 is a perspective view showing, as partially broken away, a sanitary napkin.

Referring to FIG. 1, a sanitary napkin 1 comprises a liquid-permeable topsheet 2, a liquid-impermeable backsheet 3 and an absorbent core 4 sandwiched between sheets 2, 3. Topsheet 2 entirely envelops the absorbent core 4 with opposite side edges thereof being overlapped and sealed together on the backside of the napkin 1 and edge portions extending along longitudinally opposite ends of the napkin 1 being also sealed together. The backsheet 3 is interposed between the topsheet 2 lying on the backside of the napkin 1 and the absorbent core 4.

Figure 2:
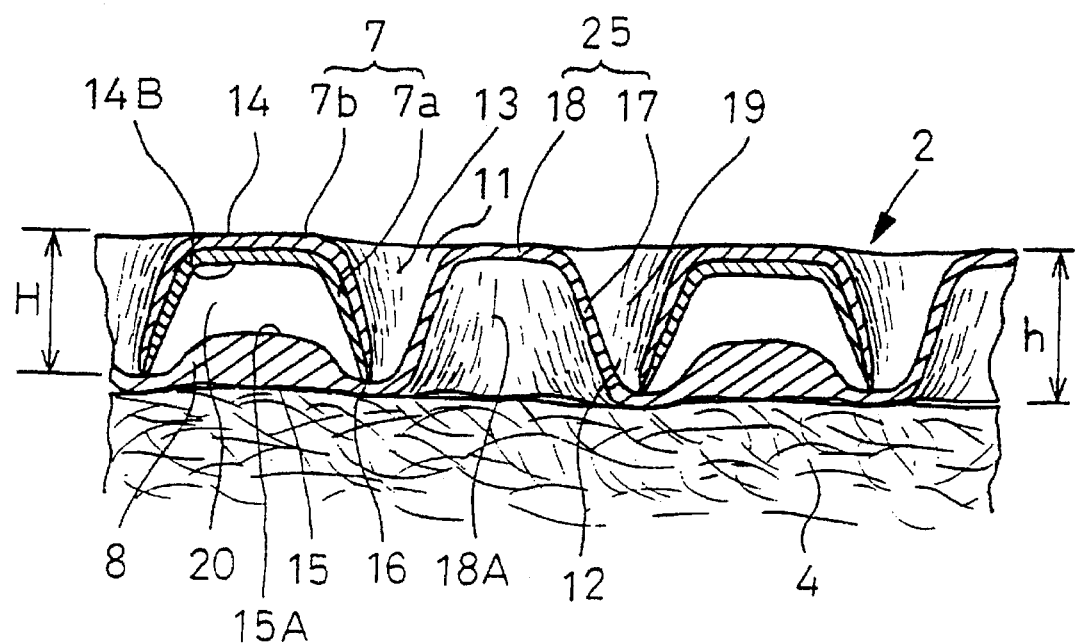
FIG. 2 is a sectional view partially showing a topsheet in an enlarged scale.

Referring to FIG. 2, the topsheet 2 is schematically illustrated in a partial section cut in the direction of its thickness. As illustrated, the absorbent core 4 is in close contact with the underside of the topsheet 2. The topsheet 2 comprises an upper sheet 7 in the form of nonwoven fabric which comprises, in turn, an integral laminate of a first layer 7a and a second layer 7b both made of melt-blown fibres, and a lower sheet 8 underlying the upper sheet 7 and made of melt-blown nonwoven fabric. While the upper sheet 7 is described herein as a two-layered sheet, the upper sheet 7 may be formed as the single-layered sheet comprising any one of the first layer 7a and said second layer 7b.

The upper sheet 7 has upper openings 11 and lower openings 12. The upper sheet 7 further includes a plurality of liquid passages 13 each extending through the sheet 7 from the upper opening 11 to the lower opening 12 and a skin-contacting area 14 which is formed as a continuous planar zone extending around the respective upper openings 11. The density and/or fineness of the first layer 7a may be selected to be higher than those of the second layer 7b to enhance the firmness of the upper sheet 7, and to maintain the soft touch of the second layer 7b.

The lower sheet 8 includes a skin-noncontacting area 15 opposed to the skin-contacting area 14 of the upper sheet 7, an area 16 bonded to peripheral edges of the lower openings 12 and an area 25 exposed within the liquid passages 13. The upper sheet 7 and the lower sheet 8 are integrated with each other by means of welding and/or mechanical intertwinement around the respective lower openings 12. An upper side 15A of the skin-noncontacting area 15 is spaced from an underside 14B of the skin-contacting area 14, so the sheets 7, 8 cooperate with the inner walls of the liquid passages 13 to define cavities 20. The exposed area 25 rises up into the respective liquid passages IS and is truncated-cone- or cone-shaped as viewed in a section cut in the direction of the topsheet thickness. The exposed area 25 has a side wall 17, an apex 18 and a height h approximately equal to or smaller than a height H of the liquid passages 13. Accordingly, the apex 18 is substantially coplanar with the skin-contacting area 14 or slightly lower than the skin-contacting area 14, and not only the skin-contacting area 14 but also the apex 18 come in contact with the wearer's skin under a body pressure exerted on the skin-contacting area 14. A V-shaped groove 19 is defined between the side wall 17 and the wall of the associated liquid passage 13. Inside the truncated-coneshape, i.e., between the apex 18 and the absorbent core 4, a space 18A is defined, within which there is little or no extending fibres of the first sheet 7a and the absorbent core 4. The skin-noncontacting area 15 is in contact with the absorbent core 4 comprising a mixture of fluff pulp and high absorption polymer powders.

In the topsheet 2, both the upper openings 11 and the lower openings 12 of the respective liquid passages 13 may be selectively configured, for example, as circular, elliptical, polygonal, indeterminate shaped openings. For example, with the liquid passages 13 each having upper and lower openings which are circular shaped, it is preferred that the upper opening 11 has a diameter of 0.5 to 5 mm at an opening/area ratio of 20 to 80% and each liquid passage 13 has a height H of 0.1 to 5 mm. The lower opening 12 may have a diameter larger or smaller than the diameter of the upper opening 11. The fineness of the melt-blown fibres forming the melt-blown nonwoven fabric of the second layer 7b and the lower sheet 8 is preferably in the order of 0.01 to 1 denier in order to assure the soft touch but the fineness of melt-blown fibres forming the first layer 7a may be 1 denier or higher. The topsheet 2 can present an air-permeability so far as there are interstices among the fibres. When such air-permeability is not required, the upper sheet 7 as a whole may be formed by a plastic sheet rather than by a melt-blown nonwoven fabric or only the first layer 7a may be formed by such plastic sheet. In such a case, the surface of the sheet may be embossed to make it rough, if necessary.

Figure 3:
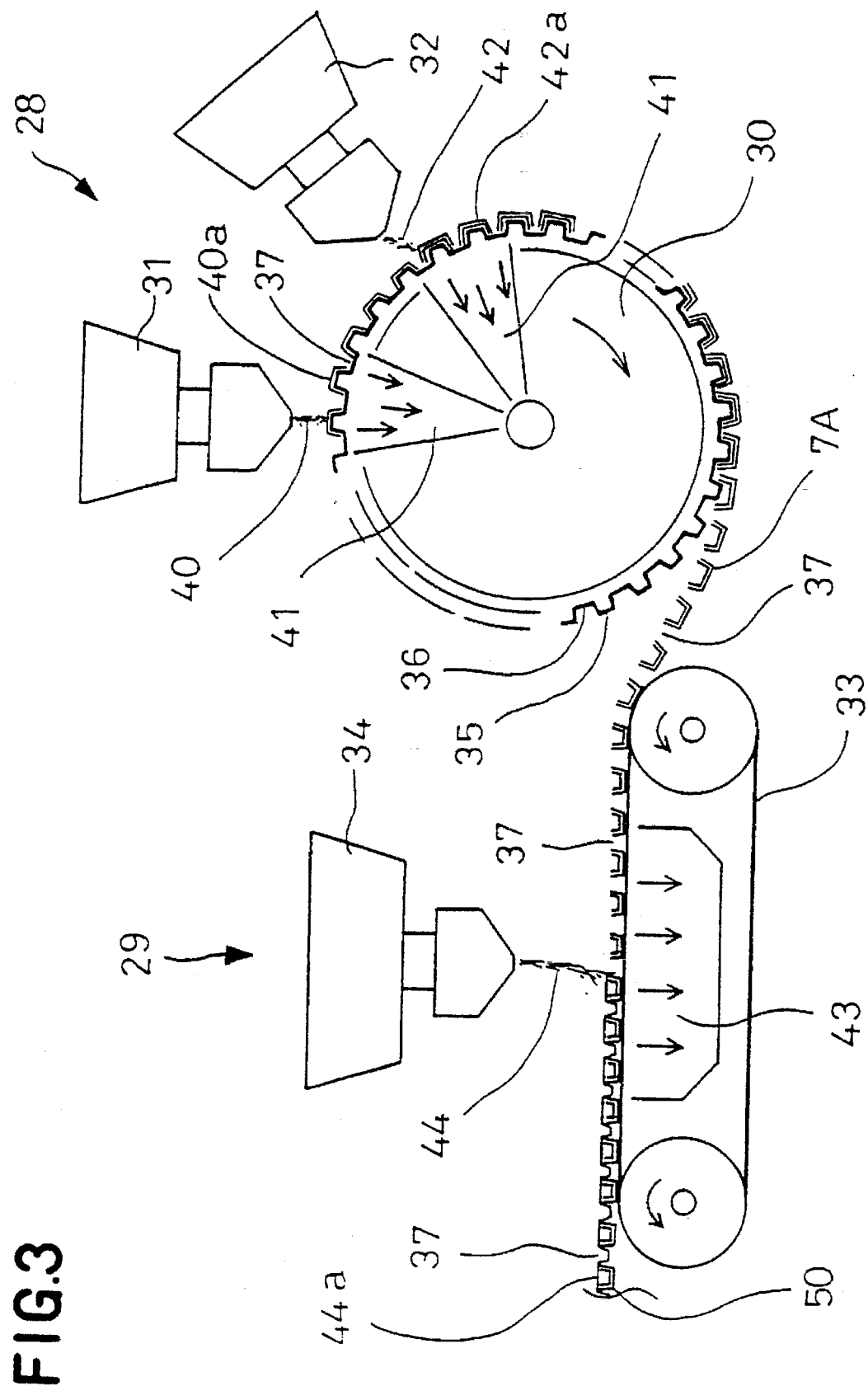
FIG. 3 is a schematic diagram illustrating a topsheet manufacturing process.

Referring to FIG. 3, a process of manufacturing the topsheet 2 is schematically illustrated. The process comprises a first molding step 28 utilizing a molding drum 30 and first and second melt-blow extruders 31, 32 provided around the molding drum 30 and a second molding step 29 utilizing an endless belt 33 and a third melt-blow extruder 34 provided above the endless bole 32. It should be understood that, when it is desired to form the first sheet 7 as the single-layered sheet, any one of the first and second meltblow extruders 31, 32 may be suspended.

In the first process 28, the molding drum 30 is provided around its outer peripheral surface with protrusions 35 and indents 36 which are alternately arranged and serve as forming dies so that melt-blown fibres 40 are blown from the first melt-blow extruder 31 against the forming dies under the effect of sections 41 to form a nonwoven fabric layer 40a destined to be the first layer 7a of the first sheet 7. Similarly, melt-blown fibres 42 are blown from the second melt-blow extruder 32 against the nonwoven fabric layer 40a to form a nonwoven fabric layer 42a destined to be the second layer 7b of the first sheet 7. A laminate of these nonwoven fabric layers 40a, 42a is then molded by the drum 30 to obtain a roll 7A of the first sheet 7 having skin-contacting area 14 formed by the protrusions 35 and the liquid passages 13 formed by the indents 36. It should be understood that various factors such as respective amounts of the fibres 40, 42 to be blown, the intensity of respective sections 41 and the depth of each indent 36 may be adjusted during the first molding process 28 so that the fibres 40, 42 may extend upward along side walls of the respective indents 36 so as to form the liquid passages 13 and may get Loose at bottoms of the respective indents 36 so as to form openings 27 destined to be the lower openings 12 of the first sheet 7. Inner and outer surfaces of the molding drum 30 are air-permeable.

The roll 7A is separated from the peripheral surface of the molding drum 30 as it is transferred from the first molding process 28 to the second molding process 29, and laid on the endless belt 33 with its surface which has contacted the peripheral surface of the molding drum 30 facing upward. Under the effect of suction 43, melt-blown fibres 44 are blown from the third melt-blow extruder 34 against the surface facing upward to form a nonwoven fabric layer 44a destined to be the second sheet 8. The amount of the fibres 44a to be blown and the intensity of the suction 43 may be adjusted to assure that the fibres 44 are exposed at the openings 37, extending upward into the liquid passages 13 and, if it is necessary, the forward end of the melt-blown nonwoven fabric layer 44a may come in contact with the upper surface of the endless belt 33 to form a planar layer defining the apex 18 as well as the space 18A of the lower sheet 8. It should be understood that the effect of the suction 43 may be attenuated to reduce or practically eliminate the rise-up of the melt-blown nonwoven fabric and such product also may be used as the topsheet 2.

Figure 4:
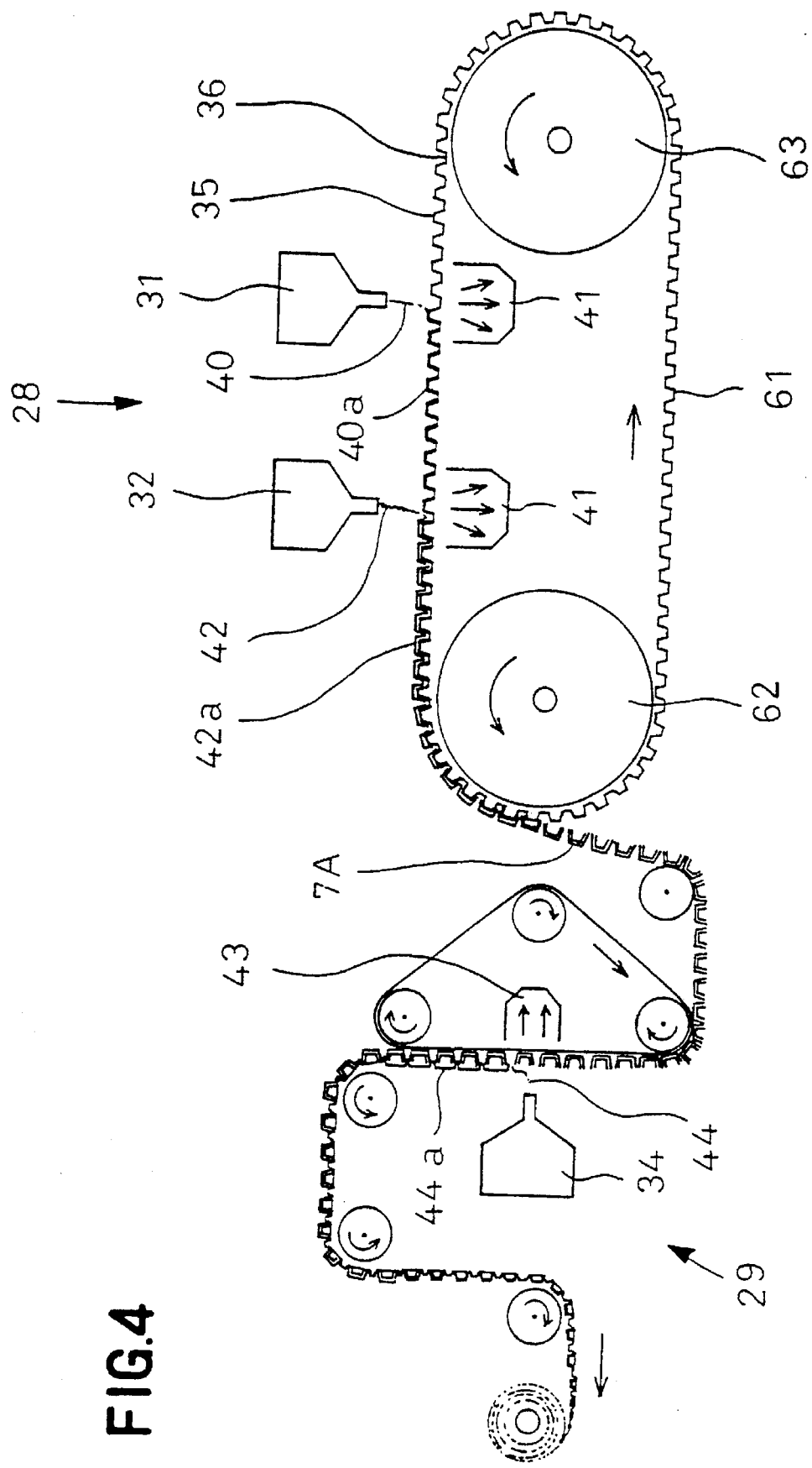
FIG. 4 is a diagram similar to FIG. 3 but showing an alternative layout of the topsheet manufacturing process.

FIG. 4 illustrates an alternative process for manufacturing the topsheet 2 which is somewhat different from the process illustrated by FIG. 3. Referring to FIG. 4, molding drum 30 is replaced by an endless belt 61 provided with the protrusions 35 and the indents 36 which are alternately arranged and serve as forming dies to form the melt-blown nonwoven fabrics 40a, 42a and the endless belt 61 is counterclockwise rotated by driving rolls 62, 63. The remainder of this process is substantially similar to that illustrated by FIG. 3. When the first and second melt-blow extruders 31, 32 are too large to install them at closely adjacent locations, it will be convenient to employ this endless belt 61.

In both processes illustrated by FIGS. 3 and 4, the melt-blown fibres 40, 42 forming the first or upper sheet 7 are fluffed around the lower openings 12 in the direction of the suction 41. The melt-blown fibres 44 blown from the third melt-blow extruder 34 against this upper sheet 7 are welded to and/or twist about the other melt-blown fibres 40, 42 and thereby integrate the second or lower sheet 8 with the upper sheet 7. In both processes illustrated, the lower layer 40a of melt-blown nonwoven fabric having a higher density or fineness is first formed in order to make the topsheet 2 firm and then the upper layer 42a of melt-blown nonwoven fabric having a lower density or fineness is formed in order to provide the topsheet 2 which can give its wearer a cloth-like soft touch.

Figure 5:
FIG. 5 is a magnified microscopic photo showing a section of the topsheet.

FIGS. 5 through 8 are magnified microscopic photos of the topsheet 2 produced by the process illustrated by FIG. 3. Referring to FIG. 5 corresponding to FIG. 2 and showing a section of the topsheet 2, the lower sheet 8 underlies the upper sheet 7 which is provided with the skin-contacting area 14 and the liquid passages 13, and the lower sheet 8 includes the skin-noncontacting area 15 and the truncated-cone- or cone-shaped exposed area 25 which defines the space 18A therein. Mutually opposing inner surfaces of the skin-contacting area 14 and the skin-noncontacting area 15 are spaced from each other and cooperate with the wall of the associated liquid passage 13 to form the cavity 20.

Figure 6:
FIG. 6 is a magnified microscopic photo showing upper openings and apices of liquid passages in the topsheet.

FIG. 6 is a magnified microscopic photo of the topsheet 2 showing, in details, the skin-contacting area 14, the upper openings 11 of the upper sheet 7 and the apex 18 of the lower sheet 8 as viewed from obliquely above.

Figure 7:
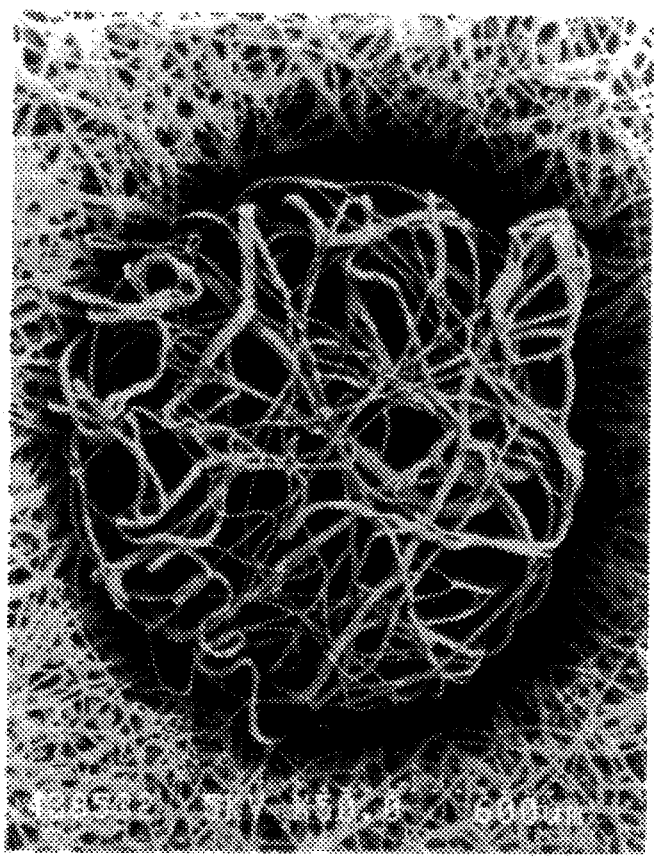
FIG. 7 is a magnified microscopic photo showing the upper openings as viewed from right above.

FIG. 7 is a photo of the topsheet 2, magnified 50×, as viewed from right above. As shown, the upper sheer 7 and the apex 18 respectively comprise the melt-blown fibres, the apex 18 presenting a fibre distribution density lower than in the upper sheet 7.

Figure 8:
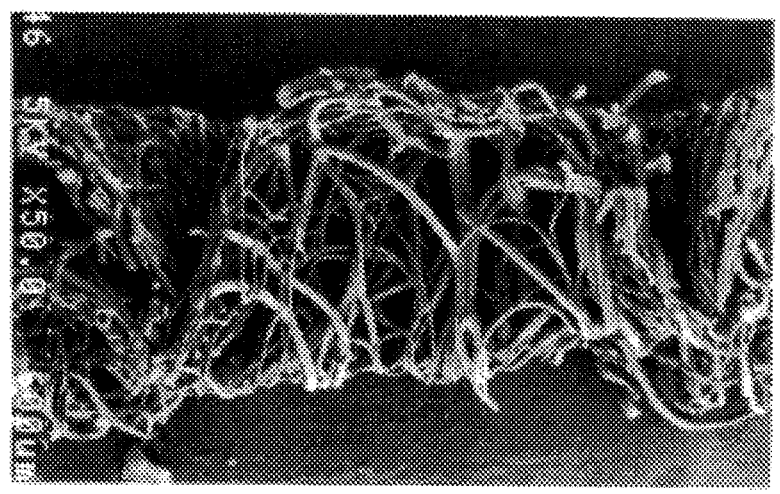
FIG. 8 is a magnified microscopic photo showing the liquid passages.

FIG. 8 is a magnified photo (50×) of the topsheet 2 in a section cut in the direction of its thickness, showing the liquid passages 13 and the truncated-cone-shaped exposed area 25 of the lower sheet 8. Though inadequately clear, it will be seen that the wall of liquid passage 13 is two-layered, i.e., consists of the melt-blown nonwoven fabrics 7a, 7b; the lower sheet 8 is welded to and/or twist about the upper sheet 7 around the lower openings 12 of the liquid passages 13; the V-shaped groove 19 is formed by the side wall 17 of the exposed area 25 and the adjacent wall of the liquid passage 13; and the apex 18 of the exposed area 25 is substantially coplanar with the skin-contacting area 14.

Instead of using the above-mentioned melt-blown nonwoven fabric, it is also within the scope of the invention to form the upper sheet 7 which is the important component of the topsheet 2 by using the nonwoven fabric made of other thermoplastic synthetic resin fibres or thermoplastic synthetic resin sheet. Preferably, the upper sheet 7 is made from suitable hydrophobic material so that a dry touch may be maintained even after the excretion of body fluids, and the lower sheer 8 can be formed also from hydrophilic thermoplastic synthetic resin nonwoven fabric other than the melt-blown nonwoven fabric so that the body fluids may be transferred toward the absorbent core and at the same time extensively spread over the lower sheet 8 as rapidly as possible. Such hydrophilic nonwoven fabric destined to form the lower sheet 8 may be obtained, for example, by coating the nonwoven fabric made of polyolefins such as polyethylene and polypropylene or polyesters with 0.1% aqueous solution of hydrophilicity giving agent such as fatty acid alkyd amide cationic agent or by homogeneously mixing any one of said synthetic resins with 0.3 to 1.0 w % of hydrophilicity giving agent such as glycerin monostearate and by using this mixture as starting material for the desired nonwoven fabric.

Instead of using such hydrophilicity giving agent, it is also possible to employ, as the lower sheet 8, the nonwoven fabric obtained from starting material as follows: ethylene-olefin copolymer having a density less than 0.900 g/cm$^3$ and a degree of crystallinity of 5 to 40% or resinous composition containing this copolymer as its main ingredient, for example, the ethylene-olefin copolymer of 100 parts by weight blended with resin of parts by weight less than 100 such as low, medium or high density polyethylene, linear low density polyethylene, polypropylene, polybutene-1, or ethylene-vinyl acetate copolymer.

A specific example of the ethylene-olefin copolymer has 3 to 10 carbons in its -olefin, ethylene content of 85 to 95 mol %, melt flow rate (MFR) of 1 to 200 g/10 min measured under a load of 2160 g at 190° C. (according to ASTM D1238), a density of 0.870 g/cm$^3$ to 0.900 g/cm$^3$ and a degree of X-ray crystallinity of 5 to 40%. The nonwoven fabric such as melt-blown nonwoven fabric obtained from the above-mentioned resin or resinous composition is not only hydrophilic but also soft and stretchable, so particularly suitable for the material of the lower sheet 8. It should be understood that the ethylene-olefin copolymer or the resinous composition containing this copolymer as its main ingredient or the sheet of nonwoven fabric or the like obtained therefrom may be treated with said hydrophilicity giving agent to further enhance its hydrophilicity.

In the topsheet constructed according to the invention, the liquid passages are effectively shape-stabilized and difficult to be blocked, since the lower sheet is welded to and/or twist about the upper sheet around the lower openings of the respective liquid passages.

The cavity defined between the upper sheet and the lower sheet serves to prevent the body fluids from flowing back to the upper sheet even when the lower sheet is wetted with the body fluids spreading over the lower sheet, so the absorptive articles employing this topsheet never give the wearer the unpleasant feel of wetness.

The body fluids excreted over the topsheet rapidly reach the lower openings of the liquid passages under the effect of capillary phenomenon occurring between each pair of the adjacent wall of the liquid passage and side wall of the exposed area rising up into the liquid passage, then partly pass through the lower sheet and are absorbed by the spot of the absorbent core which immediately underlies the lower opening of this liquid passage, partly spread over the lower sheet and are absorbed by the remainder portion of the absorbent core being in contact with the skin-noncontacting area of the lower sheet. In this manner, the topsheet of the invention allows the absorption rate to be improved over the topsheet of prior art merely provided with the liquid passages.

If the apex formed by the portion of the lower sheet rising up into the liquid passage is composed of hydrophilic nonwoven fabric adapted to come in contact with the wearer's skin, said capillary phenomenon serves also to transfer sweat when the wearer is sweaty, Accordingly, even when the upper sheet is made of hydrophobic plastic film, the topsheet can be sweat-absorptive. While the apex may possibly absorb some quantity of moisture from the absorbent core under the capillary effect, such quantity of moisture absorbed back can be minimized by the space defined between the apex and the absorbent core.

High shape-stability of the liquid passages improves a cushioning effect and therefore comfortableness of wearing the absorptive articles.

The topsheet can be easily manufactured, since the melt-blown nonwoven fabric is formed merely by blowing molten fibres against the underside of the upper sheet.

With the apparatus of the invention for making the topsheet, the upper sheet is formed by the first and second melt-blow extruders exclusively used to form the first and second sheets, respectively and then the lower sheet is formed by blowing molten fibres from the third melt-blow extruder against the underside of the upper sheet, thus allowing the topsheet to be continuously produced.

What is claimed is:

1. A method for making a topsheet for use in body fluid absorptive articles, said topsheet being provided with a plurality of liquid passages each extending through the topsheet from an upper opening to a lower opening thereof and a skin-contacting area continuously formed around the upper openings of the respective liquid passages, said method comprising the steps of:

forming a first sheet provided with said liquid passages and said skin-contacting area from a thermoplastic sheet and blowing molten fibres onto a lower side of said first sheet to form a second sheet made of melt-blown nonwoven fabric, wherein said second sheet has a skin-non-contact area spaced from a lower surface of the skin-contacting area defined by said first sheet and an area welded to said liquid passages around their lower openings, said second sheet also having an exposed area within said liquid passages, each exposed area having a side wall and an apex rising up into each of said liquid passages a height of approximately equal to a distance between the upper opening and the lower opening without extending above an upper surface of the skin-contacting area and wherein inner walls of said liquid passages and said second sheet cooperate to define cavities extending in the direction of the topsheet's thickness.

* * * * *